United States Patent [19]

Tjan

[11] Patent Number: 4,863,463
[45] Date of Patent: Sep. 5, 1989

[54] ARTIFICIAL INTRA-OCULAR LENS FOR IMPLANTATION IN THE CAPSULAR BAG

[76] Inventor: Tik T. Tjan, Benoordenhoutseweg 236, 2596 BG Den Haag, Netherlands

[21] Appl. No.: 206,511

[22] Filed: Jun. 14, 1988

[30] Foreign Application Priority Data

Dec. 21, 1987 [NL] Netherlands .......................... 8703089

[51] Int. Cl.⁴ .............................................. A61F 2/16
[52] U.S. Cl. ...................................................... 623/6
[58] Field of Search ............................................. 623/6

[56] References Cited

U.S. PATENT DOCUMENTS

4,636,212 1/1987 Posin et al. .............................. 623/6
4,681,586 7/1987 Woods ..................................... 623/6

FOREIGN PATENT DOCUMENTS

8500527 1/1986 Netherlands ............................. 623/6

OTHER PUBLICATIONS

"Lens Styles from Cilco", Advertisement Brochure, 6 pages, Oct. 1982.
"New Concepts in Circular Posterior Chamber Lenses", OSN Interview, Ocular Surgery News, Oct. 1, 1987, pp. 16–18.

*Primary Examiner*—Ronald L. Frinks
*Attorney, Agent, or Firm*—Peter L. Michaelson

[57] ABSTRACT

An artificial intra-ocular lens to be substituted for a natural lens which has been clouded by cataract. The lens is designed to be placed in the capsular bag from which the nucleus and cortex of the clouded lens have been removed. According to the invention the lens has a closed ring (3) extending concentrically about an optic component (2). The ring is connected to the periphery of the optic component (2) by means of two arms (4, 4') each extending circumferentially between the optic component (2) and the circumferential ring (3) and being connected to the periphery of the optic component (2) and to the ring (3) by means of arm ends (6, 6') and (5, 5'), respectively. These arm ends extend in fan-shaped configuration perpendicularly to the periphery of the optic component (2) and to the circumferential ring, respectively. Each arm end (6, 6') connected to the periphery of the optic component (2) is offset by an angle of 15°–20° relatively to the end (5', 5) of the other arm connected to the circumferential ring.

10 Claims, 2 Drawing Sheets

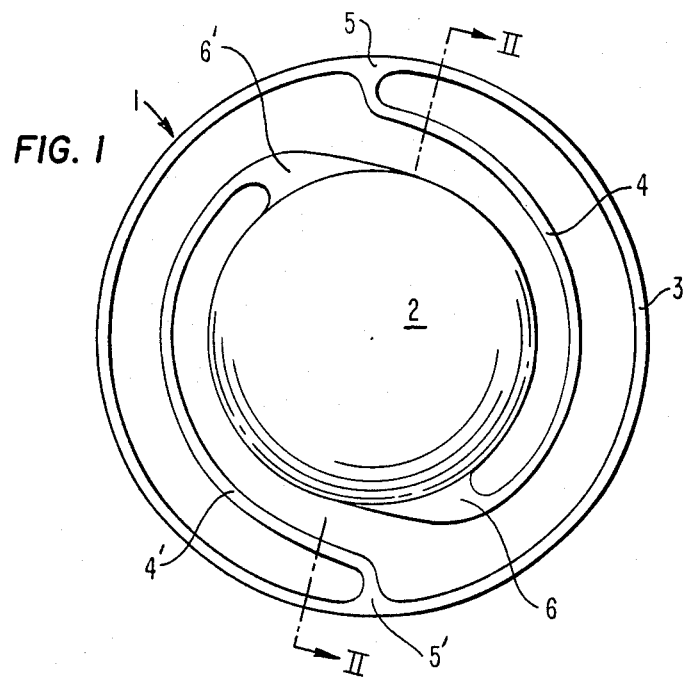
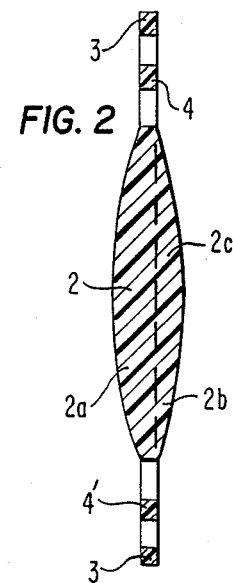
FIG. 1
FIG. 2
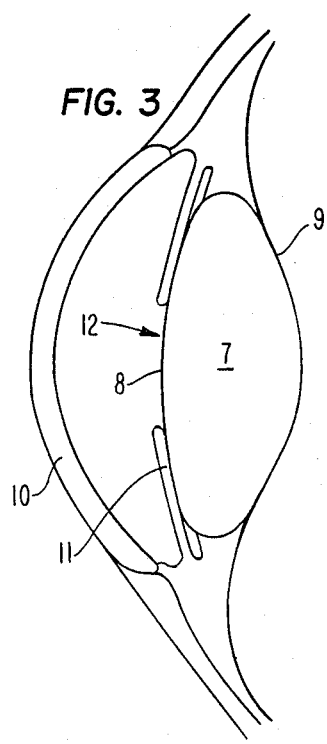
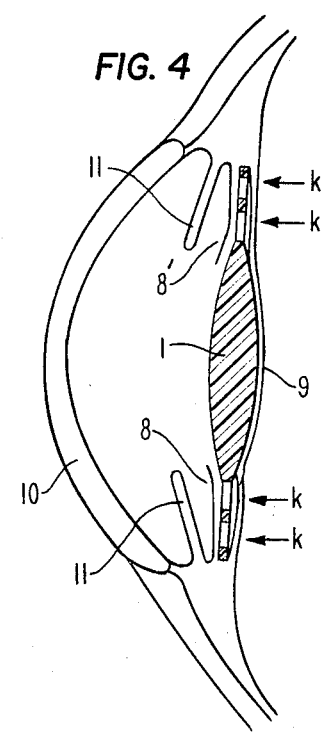
FIG. 3
FIG. 4

ARTIFICIAL INTRA-OCULAR LENS FOR IMPLANTATION IN THE CAPSULAR BAG

BACKGROUND OF THE INVENTION

This invention relates to an artificial lens to be substituted for a natural lens clouded by cataract, said artificial lens being designed to be placed in the space formed by the capsular bag of the lens. This space is produced by the removal of the nucleus of the clouded lens and the cortical remnants.

The implantation technique comprises the maximal dilation of the pupillary aperture by chemical means, making an incision along the upper rim of the cornea, and opening the anterior lens capsule at the level of the upper quadrant by means of a horizontal incision slightly curved towards the eye axis. After expression of the natural lens nucleus a space for receiving the artificial lens is available in the capsular bag which is situated between the anterior and the posterior lens capsule. Subsequently, the collapsed capsular bag is filled with a visco-elastic substance, as is the portion of the capsular bag situated above the incision. Thus an oval gaping hole is produced through which the artificial lens can pass to reach the capsular bag.

The artificial lens has to pass three apertures when being placed in the capsular bag, i.e. the incision along the upper rim of the cornea, the pupillary aperture, which is variable, and the incision in the anterior capsule.

The artificial lens has an optic component of a material (PMMA=polymethyl methacrylate) which is inert in living tissue, as has been proven over the years. This optic portion is smaller than the cataractous lens, so that rentering and anchoring means generally called haptics, (such as a ring, arms, loops, etc.) are required to maintain the lens centrally behind the pupil.

The great flexibility of the arms and ring enables the artificial lens to pass through the comparatively small access aperture of the capsular bag of the lens.

SUMMARY OF THE INVENTION

It is one object of the present invention to provide an artificial lens having as centering and anchoring means, a ring and arms made from the same durable, biologically inert material as the optic component. It is a further object of the invention to provide an artificial lens which, by virtue of its configuration, has a flexibility and deformability which facilitates its implantation in the capsular bag. This is due in part because the optic component and the ring with the arms maintain a co-planar relationship when radial forces are exerted on the ring.

To that end, according to the present invention, the centering and anchoring means comprise a closed ring extending substantially concentrically about the optic component, said ring being connected to the periphery of the optic component by means of two arms, each extending circumferentially between the optic component and the circumferential ring, said arms being connected to the periphery of the optic component and to the circumferential ring through arm ends extending in fan-shaped configuration perpendicularly to the periphery of the optic component and the circumferential ring, respectively, each arm end connected to the periphery of the optic component being offset by an angle of 15°-20° relatively to the end of the other arm connected to the circumferential ring.

The closed circumferential ring, without protruding portions, reduces the risk of perforation of the posterior lens capsule during insertion. Local, radially inward forces on the ring which flex it inwards, basically only produce a rotation of the optic component in its own plane and not its deflection from this plane in directions perpendicular thereto. Consequently, the artificial lens according to the present invention, can be implanted with greater ease.

The outside diameter of the artificial lens of about 10 mm can be locally narrowed down to at least 8 mm without the optic component moving out of its plane. By virtue of this feature, the size of apertures can be minimized.

The rigidity required for maintaining the ring, the connecting arms and the optic component in co-planar relationship, that is to say, the rigidity perpendicular to that plane, is provided by the rigid, fan-shaped connections of the arms to the periphery of the optic component and of the arm ends of the ring.

BRIEF DESCRIPTION OF THE DRAWINGS

One embodiment of the artificial intra-ocular lens according to the present invention will now be described, by way of example, with reference to the accompanying drawings, in which:

FIG. 1 is a top view of the artificial lens;

FIG. 2 is a cross-sectional view taken on the line II—II of FIG. 1;

FIG. 3 is a vertical cross-sectional view of a detail of a healthy eye;

FIG. 4 is a cross-sectional view similar to FIG. 3 with an implanted lens; and

DESCRIPTION OF THE PREFERRED EMBODIMENT

Figure 5:
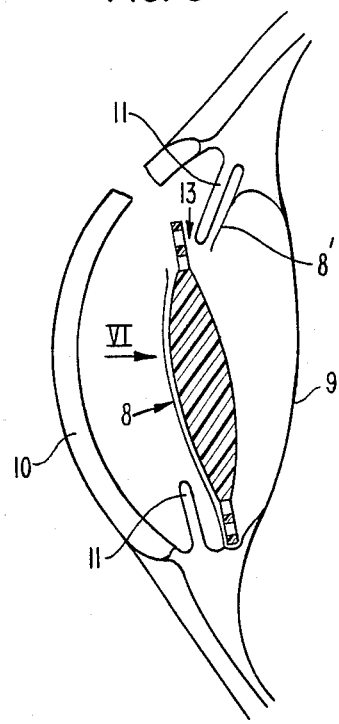
FIGS. 5 and 6 show the principle of the implantation of an intra-ocular lens.

As shown in FIGS. 1 and 2, an intra-ocular lens 1 includes an optic component or lens body 2 and centering and anchoring means comprising a concentric ring 3 and two connecting arms 4, 4' extending along the major part of their lengths circumferentially between the lens body 2 and the ring 3. Arms 4, 4' are connected through arm ends 5, 5' and 6, 6', respectively, extending in fan-shaped configuration, perpendicularly to the ring and to the periphery of the lens body 2, to diametrically opposite places near the ring and near the periphery of lens body 2. Each arm end 6, 6' with which arm 4, 4' is connected to the periphery of lens body 2, is offset by an angle of 15°-20° relatively to arm end 5', 5 with which the other arm 4', 4 is connected to ring 3.

The optic component (lens body 2) is illustratively biconvex, i.e. surfaces 2a and 2b are both convex, with a diameter of approximately 6 mm. Alternatively, lens body 2 can also be plano-convex in shape, in which case the lens body would be bounded by convex surface 2a and flat surface 2c, the latter surface existing in lieu of convex surface 2b.

FIG. 3 is a detail view of a normal eye with a lens 7 confined in a capsule whose anterior portion is indicated at 8 and its posterior portion at 9. FIG. 3 also shows the cornea 10 and the iris 11 defining the variable pupillary aperture 12.

FIG. 4 shows the eye detail of FIG. 3, wherein the original lens cortex and nucleus have been replaced by an intra-ocular lens 1. Arrows K indicate the places where anterior and posterior capsular tissues adhere to each other, thereby fixing ring 3 and arms 4, 4' and retaining the lens body 2 centrally behind the pupil.

Figure 6:
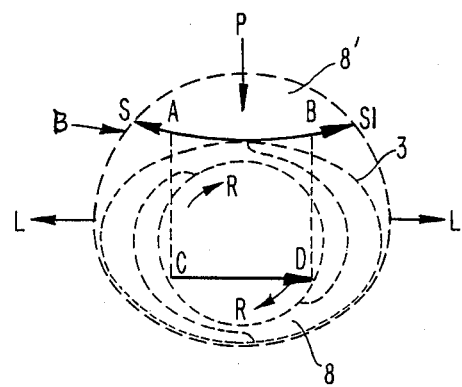

FIG. 6 is an elevational view according to the arrow VI of FIG. 5 and these figures show the phase of the introduction of the intra-ocular lens 1 into the empty capsular bag. In the anterior lens capsule 8 an incision 13 has been made slightly curved convexly towards the optic axis between the points S and S1. The length of this incision is slightly smaller than the diameter of the circumferential ring 3 of the lens. Consequently, ring 3 should be temporarily narrowed for it to pass incision 13. Such a constriction is concomitant with a rotation of the lens 2 in its own plane, as indicated with arrows R—R in FIG. 6.

In order to bring the upper portion of the lens body 2 and of ring 3 behind the portion 8' of the anterior lens capsule 8 situated above incision 13, pressure is exerted on ring 3 according to arrow P, which results in a lateral deformation according to arrows L. The distance 5, 5' (FIG. 1) becomes smaller and the upper portion of the ring can be inserted into the capsular bag portion situated above the incision 13.

When the intra-ocular lens has thus been placed in position, the anterior lens capsule is incised in the points A and B up to the points C and D. Subsequently, the flap is severed from C to D to form a window A, B, C, D.

For the manufacture of the intra-ocular lens 1, a biconvex lens can be turned from a disc of a suitable material, such as PMMA, with a radial circumferential flange from which ring 3 and arms 4, 4' can be formed by removing material.

In this instance, since the entire intra-ocular lens is formed from the same disk, i.e. one-piece, of PMMA, the PMMA used to form this disk could contain either UV (ultraviolet) absorbing substances or no such absorbing substances. Alternatively, the intra-ocular lens could be formed with a optic component made from PMMA while the ring and both arms are made from polypropylene.

I claim:

1. An artificial intra-ocular lens to be substituted for a natural eye lens which has been clouded by cataract, said artificial lens being designed to be placed in the lens capsule from which the nucleus and cortex of the clouded lens have been removed, said artificial lens including an optic component having centering and anchoring means extending radially beyond its periphery, characterized in that said centering and anchoring means comprise a closed ring (3) extending substantially concentrically about the optic component (2), said closed ring being connected to the periphery of the optic component by means of two arms (4, 4') each extending circumferentially between the optic component (2) and the circumferential ring (3) and being connected to the periphery of the optic component and to the ring (3) by means of arm ends (6, 6') and (5, 5'), respectively, extending in fan-shaped configuration, perpendicularly to the periphery of the optic component, and to the circumferential ring, respectively, each arm end (6, 6') connected to the periphery of the optic component being offset by an angle of 15°–20° relatively to the end (5', 5) of the other arm connected to the circumferential ring.

2. An artificial intra-ocular lens as claimed in claim 1, characterized in that the optic component (2) and the centering and anchoring means (3, 4, 4') are made in one piece from PMMA containing no UV-absorbing substances.

3. An intra-ocular lens as claimed in claim 1, characterized in that the optic component (2) and the centering and anchoring means (3, 4, 4') are made from PMMA with UV-absorbing substances.

4. An artificial intra-ocular lens as claimed in claim 1, characterized in that the optic component (2) is biconvex and has a diameter of about 6 mm and the circumferential ring (3) has a diameter of about 10 mm.

5. An artificial intra-ocular lens as claimed in claim 1, characterized in that the optic component is made from PMMA and the centering and anchoring means from polypropylene.

6. An artificial intra-ocular lens as claimed in claim 1, characterized in that the optic component has a plano-convex shape.

7. An artificial intra-ocular lens as claimed in claim 2, characterized in that the optic component (2) is biconvex and has a diameter of about 6 mm and the circumferential ring (3) has a diameter of about 10 mm.

8. An artificial intra-ocular lens as claimed in claim 3, characterized in that the optic component (2) is biconvex and has a diameter of about 6 mm and the circumferential ring (3) has a diameter of about 10 mm.

9. An artificial intra-ocular lens as claimed in claim 2, characterized in that the optic component has a plano-convex shape.

10. An artificial intra-ocular lens as claimed in claim 3, characterized in that the optic component has a plano-convex shape.

* * * * *